United States Patent
Lee et al.

(10) Patent No.: US 11,370,855 B2
(45) Date of Patent: *Jun. 28, 2022

(54) METHOD FOR PREPARING BUTENE OLIGOMER

(71) Applicant: LG Chem, Ltd., Seoul (KR)

(72) Inventors: Jin Lee, Daejeon (KR); Dong Hyun Jo, Daejeon (KR); Won Hee Kim, Daejeon (KR); Gyeong Shin Choi, Daejeon (KR)

(73) Assignee: LG Chem, Ltd.

( * ) Notice: Subject to any disclaimer, the term of this patent is extended or adjusted under 35 U.S.C. 154(b) by 133 days.

This patent is subject to a terminal disclaimer.

(21) Appl. No.: 16/644,703

(22) PCT Filed: Jul. 26, 2019

(86) PCT No.: PCT/KR2019/009331
§ 371 (c)(1),
(2) Date: Mar. 5, 2020

(87) PCT Pub. No.: WO2020/022833
PCT Pub. Date: Jan. 30, 2020

(65) Prior Publication Data
US 2020/0283550 A1    Sep. 10, 2020

(30) Foreign Application Priority Data

Jul. 27, 2018 (KR) .................. 10-2018-0087542

(51) Int. Cl.
| | | |
|---|---|---|
| C08F 10/10 | (2006.01) | |
| C08F 110/10 | (2006.01) | |
| C08F 4/52 | (2006.01) | |
| C08F 2/38 | (2006.01) | |
| C08F 6/02 | (2006.01) | |

(52) U.S. Cl.
CPC ............. C08F 10/10 (2013.01); C08F 2/38 (2013.01); C08F 4/52 (2013.01); C08F 6/02 (2013.01)

(58) Field of Classification Search
CPC .......... C08F 10/10; C08F 110/10; C08F 4/52
See application file for complete search history.

(56) References Cited

U.S. PATENT DOCUMENTS

| | | |
|---|---|---|
| 2003/0088135 A1 | 5/2003 | Yun et al. |
| 2003/0120006 A1 | 6/2003 | Bell et al. |
| 2003/0176606 A1 | 9/2003 | Bohnenpoll et al. |
| 2005/0107551 A1 | 5/2005 | Lang et al. |
| 2008/0221285 A1 | 9/2008 | Walter et al. |
| 2008/0249264 A1 | 10/2008 | Hanefeld et al. |
| 2008/0249267 A1 | 10/2008 | Hanefeld et al. |
| 2008/0293900 A1 | 11/2008 | Hanefeld et al. |
| 2009/0105432 A1 | 4/2009 | Rath et al. |
| 2010/0292422 A1 | 11/2010 | Rath et al. |
| 2014/0228206 A1 | 8/2014 | Ricci et al. |
| 2015/0105525 A1 | 4/2015 | Faust et al. |

FOREIGN PATENT DOCUMENTS

| | | |
|---|---|---|
| CN | 1333788 A | 1/2002 |
| CN | 1445249 A | 10/2003 |
| CN | 101282785 A | 10/2008 |
| CN | 101283001 A | 10/2008 |
| CN | 101283006 A | 10/2008 |
| CN | 101331154 A | 12/2008 |
| CN | 101331159 A | 12/2008 |
| CN | 101331160 A | 12/2008 |
| EP | 1915406 A1 | 4/2008 |
| EP | 3680258 A1 | 7/2020 |
| JP | 2003277428 A | 10/2003 |
| JP | 2005519155 A | 6/2005 |
| JP | 2016210940 A | 12/2016 |
| KR | 100279498 B1 | 1/2001 |
| KR | 100486044 B1 | 4/2005 |
| KR | 20080044870 A | 5/2008 |
| KR | 20080068107 A | 7/2008 |
| KR | 20080078654 A | 8/2008 |
| KR | 101233924 B1 | 2/2013 |
| KR | 20140069136 A | 6/2014 |
| KR | 20150042739 A | 4/2015 |
| WO | 2007020248 A1 | 2/2007 |
| WO | 2007057404 A1 | 5/2007 |
| WO | 2018015306 A1 | 1/2018 |

OTHER PUBLICATIONS

Ding et al., "On Approaching the Limit of Molecular Magnetic Anisotropy: A Near-Perfect Pentagonal Bipyramidal Dysprosium(III) Single-Molecule Magnet", A Journal of the German Chemical Society, Nov. 2016, pp. 16071-16074, vol. 55.

Evans et al., "Divalent lanthanide complexes free of coordinating anions: facile synthesis of fully solvated dicationic [LnLx]2+ compounds", Polyhedron, Jan. 2003, pp. 119-126, vol. 22, Issue 1.

International Search Report from Application No. PCT/KR2019/009331 dated Oct. 28, 2019, 2 pages.

Kaliner et al., "Tunable aryl alkyl ionic liquids with weakly coordinating bulky borate anion", Tetrahedron Letters, Aug. 2016, pp. 3453-3456, vol. 57, Issue 31.

Kuhn et al., "Solvent stabilized transition metal cations as initiators for cyclopentadiene polymerization", Macromolecular Rapid Communications, Sep. 1999, pp. 555-559, vol. 20.

Rach et al., "On the Way to Improve the Environmental Benignity of Chemical Processes: Novel Catalysts for a Polymerization Process", Sustainability, Mar. 2009, pp. 35-42, vol. 1, No. 1.

(Continued)

*Primary Examiner* — Catherine S Branch
(74) *Attorney, Agent, or Firm* — Lerner, David, Littenberg, Krumholz & Mentlik, LLP

(57) ABSTRACT

The present invention provides a method for preparing a butene oligomer including a step of oligomerizing a polymerization solution including a halogenated hydrocarbon solvent, a nonpolar hydrocarbon solvent and an isobutene monomer in the presence of an organometal catalyst.

16 Claims, No Drawings

(56) References Cited

OTHER PUBLICATIONS

Sakiyama et al., "Structural Feature of an Octakis-DMSO Cerium(III) Complex: Tetragonal Antiprismatic Coordination Geometry along the c Axis", X-Ray Structure Analysis Online, May 2014, pp. 19-20, vol. 30.
Sone et al., "Thermochemical Studies on the Lanthanoid Complexes of N,N,N,N-Tetramethylurea", The Chemical Society of Japan, Jul. 1981, pp. 449-452, vol. 55, No. 2.
Extended European Search Report including Written Opinion for Application No. EP19840223.2 dated Dec. 23, 2020, 9 pages.
Search Report dated Dec. 20, 2021 from the Office Action for Chinese Application No. 201980004328.1 dated Dec. 30, 2021, 3 pages.

METHOD FOR PREPARING BUTENE OLIGOMER

CROSS-REFERENCE TO RELATED APPLICATIONS

The present application is a national phase entry under 35 U.S.C. § 371 of International Application No. PCT/KR2019/009331 filed Jul. 26, 2019, which claims priority from Korean Patent Application No. 2018-0087542 filed Jul. 27, 2018, all of which are incorporated herein by reference.

TECHNICAL FIELD

The present invention relates to a method for preparing a butene oligomer.

BACKGROUND ART

Generally, in a process for preparing an oligomer or a polymer by the cationic polymerization of monomers, a propagating polymer chain includes an active moiety which has a positive charge. For example, the active moiety may be a carbenium ion (carbon cation) or an oxonium ion.

As a catalyst or an initiator for such cationic polymerization, an aluminum- or boron-based Lewis acid is generally used. Examples of the Lewis acid catalyst include $AlX_3$, $BX_3$ (X=F, Br, Cl, I), etc., and the Lewis acid is a corrosive substance and produces halogen components such as HCl and HF during a quenching process, and this halogen components remain in a product to cause problems of degrading product quality. In addition, a Lewis acid catalyst requires a large amount of catalyst, and in order to remove the catalyst after reaction, a large amount of base (NaOH, KOH, $NH_4OH$, etc.) is used, and accordingly, additional washing with water is required and a large amount of waste water is produced.

Meanwhile, examples of the monomer which is capable of undergoing cationic polymerization include styrene, isobutene, cyclopentadiene, dicyclopentadiene and the derivatives thereof, and typical examples include polyisobutene obtained by polymerizing isobutene.

Polyisobutene is classified into a low molecular weight, medium molecular weight and high molecular weight range according to the range of molecular weight. The low molecular weight polyisobutene has a number average molecular weight range of about 10,000 or less, and includes product groups of common butene oligomer and high reactive butene oligomer (HR-PB). The high reactive butene oligomer includes carbon-carbon double bonds mainly positioned at the terminal of the butene oligomer, and after introducing a functional group using a vinylidene functional group at the terminal (>80%), the high reactive butene oligomer is used as a fuel additive or an engine oil additive. In order to polymerize such high reactive butene oligomer, a boron-based catalyst such as $BF_3$ is used in the conventional technique, but this catalyst is toxic and has a gas type, and is difficult to handle. In addition, in order to increase reactivity and selectivity, a boron-alcohol or boron-ether composite is prepared and used, but there is a problem that the activity of the catalyst is reduced over time.

Meanwhile, according to a solvent-ligated organometal catalyst studied by professor Kuhn of Technical University of Munich (Macromol. Rapid Commun., vol. 20, no. 10, pp. 555-559), problems relating to the deterioration of product quality and corrosiveness due to the toxic component such as the conventional boron-based Lewis acid catalyst may be solved, but since the reaction time is fundamentally long and 16 hours for attaining high conversion ratio, structural isomerization is generated through the reaction of a portion of the product with the catalyst with the increased times, the exo-content is decreased, and the competitiveness is lower than the Lewis acid catalyst.

Meanwhile, a metal complex which has a bulky counter anion $[M(NCCH_3)_6]$ $[B(C_6F_5)_4]$, is widely used as a precursor of various catalysts, and recently receives much attention as having activity which is capable of polymerizing isobutene. Generally, in order to prepare such a compound, a metal complex is prepared using a photosensitive silver reagent, or a metal reagent of group 1 or group 2, such as lithium (Li), sodium (Na), potassium (K), and magnesium (Mg) according to the reaction below.

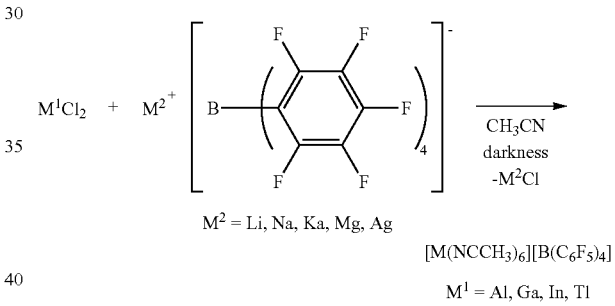

$M^2$ = Li, Na, Ka, Mg, Ag $[M(NCCH_3)_6][B(C_6F_5)_4]$ $M^1$ = Al, Ga, In, Tl

However, in the reaction, a metal salt ($M^2Cl$, $M^2$=Li, Na, Ka, Mg, Ag, etc.) is produced, and if this metal salt is incompletely removed and remain with the catalyst, the activity of the catalyst may be degraded due to poisoning. In addition, the yield is very low in the above-described method, and there are problems that a catalyst could not be prepared efficiently. Among them, a silver reagent having good reactivity is widely used, but if the silver reagent is used with a metal having a low oxidation potential, a metal may be easily oxidized, and its use is limited.

Generally, the preparation of such silver reagent follows a synthetic method according to the following Reactions (a) and (b):

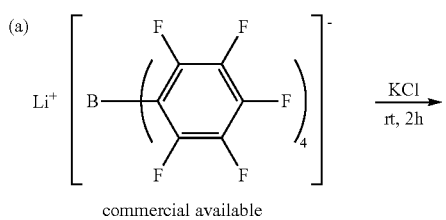

commercial available

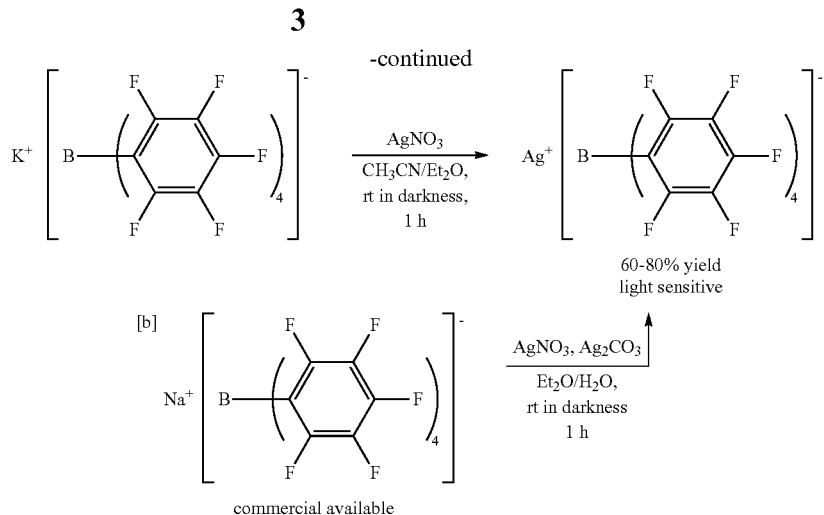

In a metal chemistry field, which is sensitive to humidity, a method using KBArF (a) is preferred to a method using NaBArF (b) as a starting material. However, both methods require the use of an expensive silver reagent material (AgNO$_3$ or Ag$_2$CO$_3$), and there are defects of relatively low yield.

Meanwhile, a cationic polymerization method which is generally used for polymerizing a polyisobutene is very sensitive to humidity and impurities, and sometimes, the reaction may be terminated due to the reaction with a small amount of humidity or impurities during the propagation of a polymer chain or chain transfer may occur, and the preparation of a polymer having a high molecular weight is difficult. In case of preparing a catalyst using the metal complex prepared using the conventional silver reagent, the complete removal of a lithium salt, a sodium salt, a potassium salt, a magnesium salt or a silver salt, which are produced during a preparation process is difficult. Accordingly, such a salt may be included in the polymerization reaction as impurities and the production of a polymer having a high molecular weight may be difficult. In addition, due to the contamination, there are defects of deteriorating the activity of a catalyst.

PRIOR ART DOCUMENTS

Patent Document (Patent Document 1) Korean Registration Patent Publication No. 10-0486044 (Apr. 29, 2005)

Non-Patent Document (Non-patent Document 1) Macromol. Rapid Commun., vol. 20, no. 10, pp. 555-559 (Sep. 16, 1999)

DISCLOSURE OF THE INVENTION

Technical Problem

The present invention uses an organometal catalyst having a cation structure including a metal in group 13 and lanthanide series and a bulky borate-based anion structure and uses a mixture solvent to solve the limitations of the conventional Lewis acid catalyst, and accordingly, a butene oligomer which is capable of controlling the molecular weight of a product in a low range, may be efficiently produced.

Particularly, an object is to provide a method for preparing a high reactive butene oligomer with the high exo-content.

Technical Solution

In order to control the number average molecular weight of a butene oligomer to less than 10,000, particularly to a desired low molecular weight range, methods of controlling the reaction temperature of a oligomerization step, controlling the amount of a catalyst, or using a molecular weight controlling agent may be applied as the conventional techniques.

However, since the reaction is mainly conducted at room temperature due to the characteristics of the catalyst used, there may be limits in controlling the molecular weight range by controlling the temperature. In addition, since most organometal catalysts of the present invention are expensive, economic burden may arise in controlling the amount of a catalyst. In addition, if a molecular weight controlling agent is added, such additive may remain in a final product to degrade its quality and to incur additional costs.

Accordingly, an embodiment of the present invention provides a method for preparing a butene oligomer including a step of oligomerizing a polymerization solution including a halogenated hydrocarbon solvent, a nonpolar hydrocarbon solvent and an isobutene monomer in the presence of an organometal catalyst represented by the following Formula 1:

[Formula 1]

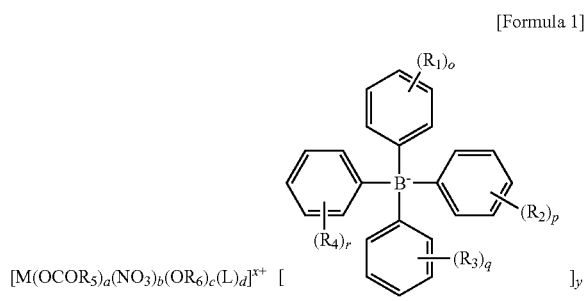

In Formula 1,

M is selected from the group consisting of metals in group 13 and lanthanide series, L is each independently a coordinating solvent molecule including a functional group selected from the group consisting of a cyanide group, an isocyanide group, an ether group, a pyridine group, an amide group, a sulfoxide group and a nitro group, $R_1$ to $R_4$ are each independently hydrogen, a halogen group, or a substituted or unsubstituted C1-C20 alkyl group, $R_5$ and $R_6$ are each independently hydrogen, a C1-C20 alkyl group, a C6-C20 aryl group, or an allyl group, a, b, c and a+b+c are each independently an integer of 0 to 3, d and a+b+c+d are each independently an integer of 1 to 10, o, p, q and r are each independently an integer of 1 to 5, and x and y are an integer of 1 to 4 and are the same.

Advantageous Effects

The method for preparing a butene oligomer of the present invention uses a mixture solvent including a halogenated hydrocarbon solvent and a nonpolar hydrocarbon solvent, and may control the molecular weight of a product to a low range and efficiently produce a butene oligomer, and in addition, toxicity due to the halogenated hydrocarbon solvent may be decreased.

In addition, according to the preparation method of the present invention, a catalyst is dissolved in a reaction product all the time and problems of arising structural isomerization reaction through the reaction with the butene oligomer may be solved and a high reactive butene oligomer with the high exo-content may be stably obtained.

Also, according the preparation method of the present invention, the catalyst may be easily removed through simple filtering without performing a washing step of the oligomer, and problems of generating a large amount of waste water in the conventional washing method and problems of degrading the quality of a product due to the remaining of the catalyst may be solved.

BEST MODE FOR CARRYING OUT THE INVENTION

Hereinafter, the present invention will be described in more detail in order to assist the understanding of the present invention. It will be understood that words or terms used in the description and claims of the present invention shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The terms used herein are for the purpose of describing particular embodiments only and are not intended to limit the present invention. The singular forms are intended to include the plural forms as well, unless the context clearly indicates otherwise.

The term "composition" used in the present disclosure includes a mixture of materials including the corresponding composition as well as a reaction product and decomposition product formed from materials of the corresponding composition.

The term "oligomerization" used in the present disclosure means the oligomerization of olefin. According to the number of olefins polymerized, the oligomerization is called as trimerization, or tetramerization, and the generic term thereof is multimerization.

The term "oligomer" used in the present disclosure means a low polymer formed by oligomerizing a monomer and having a number average molecular weight in a range of less than 10,000.

The term "polymer" has relative concept to the oligomer and means a polymer compound formed by polymerizing a monomer and having a number average molecular weight of 10,000 or more.

The term "alkyl group" in the present invention may mean a monovalent aliphatic saturated hydrocarbon, and may include a linear alkyl group such as methyl, ethyl, propyl and butyl, and a branched alkyl group such as isopropyl, sec-butyl, tert-butyl and neo-pentyl.

The term "aryl group" in the present invention may mean a cyclic aromatic hydrocarbon, and may include both monocyclic aromatic hydrocarbon in which one ring is formed, and polycyclic aromatic hydrocarbon in which two or more rings are formed.

The term "allyl group" in the present invention means a substituent having a formula of $H_2C=CH-CH_2R$, where R means the remaining moiety of the substituent.

The terms "comprising", "including", and "having" and the derivatives thereof in the present invention, though these terms are particularly disclosed or not, do not intended to preclude the presence of optional additional components, steps, or processes. In order to avoid any uncertainty, all compositions claimed by using the term "comprising" may include optional additional additives, auxiliaries, or compounds, including a polymer or any other materials, unless otherwise described to the contrary. In contrast, the term "consisting essentially of ~" excludes unnecessary ones for operation and precludes optional other components, steps or processes from the scope of optional continuous description. The term "consisting of ~" precludes optional components, steps or processes, which are not particularly described or illustrated.

1. Preparation Method of Butene Oligomer

An embodiment of the present invention provides a method for preparing a butene oligomer including a step of oligomerizing a polymerization solution including a halogenated hydrocarbon solvent, a nonpolar hydrocarbon solvent and an isobutene monomer in the presence of an organometal catalyst represented by Formula 1.

The method for preparing a butene oligomer of the present invention is characterized in performing a oligomerizing step by using a mixture solvent including a halogenated hydrocarbon solvent; and a nonpolar hydrocarbon solvent. In this case, effects of decreasing the toxicity of the halogenated hydrocarbon solvent may be achieved when compared to a case of using the halogenated hydrocarbon solvent alone.

In addition, the polarity of a solvent influences the reactivity during polymerizing the butene oligomer, and by controlling a dielectric constant of the mixture solvent by mixing the halogenated hydrocarbon solvent with the nonpolar hydrocarbon solvent, a butene oligomer in a low molecular weight range may be obtained.

In addition, in case of using only the halogenated hydrocarbon solvent in the conventional technique, there are problems that a catalyst is dissolved in the reaction product all the time and reacts with a butene oligomer to arise structural isomerization reaction. According to the present invention, the catalyst is hardly dissolved in the nonpolar hydrocarbon solvent in the mixture solvent, and the above-described problems may be solved and a high reactive butene oligomer having the high exo-content may be stably obtained.

In addition, in case of using the halogenated hydrocarbon solvent alone, the catalyst is partially dissolved in the halogenated hydrocarbon solvent, and the removal of the catalyst from the butene oligomer product may become difficult. For example, during removing the catalyst by filtering the butene oligomer thus obtained, in case of using the halogenated hydrocarbon solvent alone, the catalyst may be dissolved in a solvent and pushed out to arise problems of contaminating a filter. However, in case of using the mixture solvent of the present invention, the catalyst is hardly dissolved in the nonpolar hydrocarbon solvent and effects of decreasing filter contamination due to pushing phenomenon may be achieved, and thus, there is economic advantage of extending the life of a filtering column.

The volume ratio of the halogenated hydrocarbon solvent and an aliphatic hydrocarbon solvent in the mixture solvent may preferably be 25:75 to 99:1, 30:70 to 85:15, 35:65 to 85:15, or 40:60 to 85:15.

If the volume ratio is satisfied, the control of the molecular weight of the butene oligomer thus produced may be easy, a butene oligomer having the high exo-content may be obtained, and the removal of the catalyst after the oligomerization step may be also easy.

If the halogenated hydrocarbon solvent is greater than the volume ratio, the controlling effect of the molecular weight of the butene oligomer, which is obtainable effect by mixing the nonpolar hydrocarbon solvent may be insignificant, and the obtaining of a butene oligomer having the high exo-content may be difficult. In addition, if the nonpolar hydrocarbon solvent is greater than the volume ratio, the halogenated hydrocarbon solvent is small and the oligomerization reaction may not be carried out well or the exo-content of the butene oligomer thus obtained may decrease.

In addition, the halogenated hydrocarbon solvent may be one or more selected from the group consisting of chloromethane, dichloromethane, trichloromethane, 1-chlorobutane and chlorobenzene.

In addition, the nonpolar hydrocarbon solvent may be an aliphatic hydrocarbon solvent or an aromatic hydrocarbon solvent. For example, the aliphatic hydrocarbon solvent may be one or more selected from the group consisting of butane, pentane, neopentane, hexane, cyclohexane, methylcyclohexane, heptane, and octane, and the aromatic hydrocarbon solvent may be one or more selected from the group consisting of benzene, toluene, xylene, and ethylbenzene.

The step of oligomerizing of the present invention may be performed by a batch type or continuous type process. In case of the continuous type process, the mixture solvent may preferably include a halogenated hydrocarbon solvent and an aromatic hydrocarbon solvent. In case of the continuous type process, a reactive monomer and a polymer may be present together and the coupling phenomenon of the butene oligomer may be carried out. If the aromatic hydrocarbon solvent is included as the nonpolar solvent, such coupling phenomenon may be controlled and a butene oligomer having the high exo-content may be obtained.

In the step of oligomerizing of the isobutene monomer, the amount of the isobutene monomer may be 1 to 50 wt %, preferably, 5 to 25 wt % based on the total weight of the polymerization solution. In addition, the amount of the catalyst may be 0.005 to 1 wt %, preferably, 0.01 to 0.025 wt % based on the total weight of the polymerization solution. If the above-described numerical ranges are satisfied, the oligomerization reaction may be efficiently performed, but if excessive amounts from the numerical ranges are injected, polymerization efficiency may not much increased in contrast to the increase of the cost of raw materials.

The organometal catalyst used in the step of oligomerizing the isobutene monomer has merits of solving various problems of the conventional Lewis acid catalyst. For example, the conventional Lewis acid catalyst is corrosive but the organometal catalyst used in the present invention is not corrosive. In addition, the organometal catalyst of the present invention requires a small amount used for obtaining equivalent degree of effects, and the catalyst cost is saved.

Particularly, the organometal catalyst used in the present invention is represented by the following Formula 1:

[Formula 1]

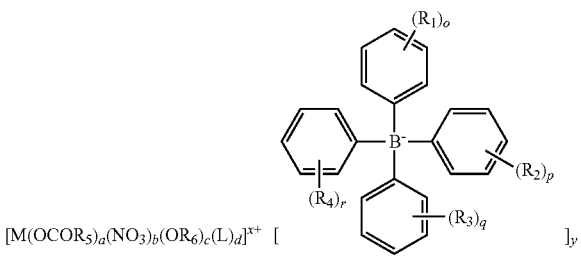

$[M(OCOR_5)_a(NO_3)_b(OR_6)_c(L)_d]^{x+}$ [ ]$_y$

In Formula 1, M is one or more selected from the group consisting of metals in group 13 and lanthanide series, and for example, may be one or more selected from the group consisting of Al, Ga, In, Tl, La, Ce, Pr, Nd, Pm, Sm, Eu, Gd, Tb, Dy, Ho, Er, Tm, Yb and Lu.

L is each independently a coordinating solvent molecule including a functional group selected from the group consisting of a cyanide group, an isocyanide group, an ether group, a pyridine group, an amide group, a sulfoxide group and a nitro group.

For example, L may be one or more selected from the group consisting of acetonitrile, propionitrile, 2-methylpropanenitrile, trimethylacetonitrile, benzonitrile, dialkyl ether, for example, diethyl ether and diallyl ether, pyridine, dimethylformamide, dimethyl sulfoxide, nitromethane, nitrobenzene and the derivatives thereof, where an unshared electron pair of oxygen, nitrogen or carbon makes a coordination bond with M.

$R_1$ to $R_4$ are each independently hydrogen, a halogen group, or a substituted or unsubstituted C1-C20, C1-C12 or C1-C4 alkyl group, preferably, a halogen-substituted C1-C4 alkyl group.

$R_5$ and $R_6$ are each independently hydrogen, a C1-C20 alkyl group, C6-C20, or C1-C12, or C6-C12, or C1-C6, or C1-C4, or C1-C2 alkyl group, a C6-C20 aryl group, or an allyl group, a, b, c and a+b+c are each independently an integer of 0 to 3, d and a+b+c+d which is related to the coordination bond number of a metal are each independently an integer of 1 to 10, o, p, q and r are each independently an integer of 1 to 5, and x and y are an integer of 1 to 4 and the same.

In the organometal catalyst, the borate-based bulky anion may be one or more selected from the group consisting of tetrakis(phenyl)borate, tetrakis(pentafluorophenyl)borate, tetrakis[3,5-bis(trifluoromethyl)phenyl]borate, and the derivatives thereof.

The organometal catalyst is characterized in not containing one or more halides of metals selected from the group consisting of the metals of group 1, group 2 and group 11. Particularly, the organometal catalyst of the present invention does not include a metal halide such as silver chloride (AgCl), lithium chloride (LiCl), sodium chloride (NaCl), potassium chloride (KCl), magnesium chloride (MgCl$_2$), silver bromide (AgBr), lithium bromide (LiBr), sodium bromide (NaBr), potassium bromide (KBr), magnesium bromide (MgBr$_2$), silver iodide (AgI), lithium iodide (LiI), sodium iodide (NaI), potassium iodide (KI), magnesium iodide (MgI$_2$) and a combination thereof.

The results are obtained because the organometal catalyst used in the preparation method of the present invention, which will be described later, is prepared by not using a metal reagent but using an organo borate-based reagent, different from the conventional technique. Accordingly, the catalyst may not induce problems of deteriorating catalyst activity and showing toxicity due to the remaining of the metal halide, and may arise efficient polymerization reaction with a small amount used to efficiently prepare an isobutene-based polymer.

The organometal catalyst used in the present invention is characterized in being prepared by a preparation method including a step of preparing a dispersion including a metal precursor represented by the following Formula 2 and a coordinating solvent; and a step of reacting an organic borate-based compound including a carbon-based, silyl-based or amine-based cation and a borate-based bulky anion, with the dispersion:

$$M(OCOR_5)_e(NO_3)_f(OR_6)_g(X)_h \qquad \text{[Formula 2]}$$

In Formula 2,

M is selected from the group consisting of metals in group 13 and lanthanide series, $R_5$ and $R_6$ are each independently hydrogen, a C12-C20 alkyl group, or a C6-C20, or C1-C12, or C6-C12, or C1-C6, or C1-C4, or C1-C2 alkyl group, a C6-C20 aryl group or an allyl group, e, f, g and h are each independently an integer of 0 to 3, and e+f+g+h is 3.

The metal precursor used in the reaction may have an anhydrous metal compound or a hydrated metal compound type, without limitation.

In an embodiment, the metal precursor may be M(NO$_3$)$_3$·B(H$_2$O), M(OAc)$_3$·B(H$_2$O), M(OR)$_3$·B(H$_2$O), M(OAc)$_{e'}$(NO$_3$)$_{f'}$, M(OAc)$_{e'}$(OR)$_{g'}$, or M(NO$_3$)$_{f'}$(OR)$_{g'}$. Here, R is each independently hydrogen or a C1-C20, or C6-C20, or C1-C12, or C6-C12, or C1-C6, or C1-C4, or C1-C2 alkyl group, aryl group or allyl group; e', f', and g' are each independently 1 or 2, e'+f', e'+g', and f'+g' are 3; and B is 1 to 10.

In addition, in the step of preparing a dispersion, the dispersion is characterized in including a Lewis base coordinating solvent. The coordinating solvent may be any solvents as long as making a coordination bond with a central metal, without specific limitation, and may be a nitrile-based solvent, for example, an alkyl cyanide or an aryl cyanide, an ether-based solvent, for example, a dialkyl ether, a pyridine-based solvent, an amide-based solvent, a sulfoxide-based solvent, or a nitro-based solvent.

For example, the coordinating solvent may include one or more selected from the group consisting of acetonitrile, propionitrile, 2-methylpropanenitrile, trimethylacetonitrile, benzonitrile, diethyl ether, diallyl ether, pyridine, dimethylformamide, dimethyl sulfoxide, nitromethane, nitrobenzene and the derivatives thereof.

In the step of preparing a dispersion of the present invention, an excessive amount of the coordinating solvent may be used with respect to the metal precursor. Preferably, the total amount of the coordinating solvent which reacts with the metal with respect to the metal precursor is controlled to achieve a molar ratio of at least 1:4, at least 1:6, at least 1:8, at least 1:12, at least 1:16, or at least 1:18. Most preferably, an amount range is controlled to achieve the molar ratio of 1:6 to 1:18, or 1:12 to 1:18.

In addition, the dispersion may further include a non-coordinating solvent, and any solvent which may dissolve the remaining metal precursor (metal salt or alkoxide) which is not used for the reaction or a material such as an organic borate and does not make a coordination bond with the metal, may be used. Examples of the non-coordinating solvent may include one or more selected from the group consisting of benzene, alkyl benzene, for example, toluene, xylene or ethylbenzene, chlorobenzene, bromobenzene, chloroform and dichloromethane.

In case where the non-coordinating solvent is used as the solvent of the dispersion, the coordinating solvent which may react with the metal precursor and be bonded as the ligand of the metal may preferably be injected in a suitable amount with the molar ratio of at least 1:6, at least 1:12, or at least 1:18 with respect to the metal precursor. Most preferably, an amount range is controlled to achieve the molar ratio of 1:6 to 1:18.

Accordingly, the method of the present invention may further include a step of adding a coordinating solvent before or after the step of reacting the organic borate-based compound with the dispersion.

In the step of reacting the organic borate-based compound containing a carbon-based, silyl-based or amine-based cation and a borate-based bulky anion, the organic borate-based compound may be represented by the following Formula 3:

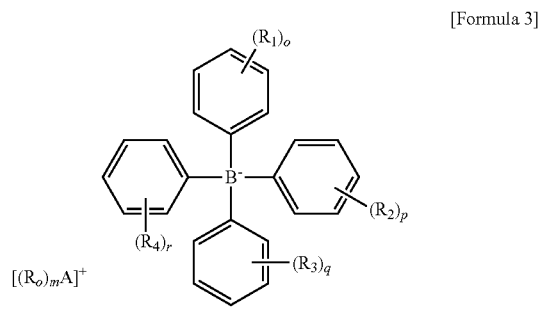

[Formula 3]

In Formula 3,

A is C, Si or N, $R_o$ is each independently hydrogen, a C1-C20 alkyl group, a C1-C20 alkoxy group, a C6-C20 aryl group, or a C6-C20 aryloxy group, preferably, hydrogen, a C1-C12 alkyl group, a C1-C12 alkoxy group, a C6-C12 aryl group, or a C6-C12 aryloxy group, more particularly, hydrogen, a C1-C6 alkyl group, or a C1-C6 alkoxy group.

m is 3 if A is C or Si, and 4 if A is N, $R_1$ to $R_4$ are each independently hydrogen, a halogen group, or a substituted or unsubstituted C1-C20 alkyl group, and o, p, q and r are each independently an integer of 1 to 5.

The borate-based bulky anion may be one or more selected from the group consisting of tetrakis(phenyl)borate, tetrakis(pentafluorophenyl)borate, tetrakis[3,5-bis(trifluoromethyl) phenyl]borate, and the derivatives thereof.

The method for preparing the organometal catalyst of the present invention is characterized in using an organic borate-based reagent which is commercially easily available and stable instead of the conventional metal reagent, for example, a silver reagent, which is photosensitive, expensive and difficult to synthesize. There were problems of remaining a metal halide together with a catalyst in the catalyst prepared by the conventional method to deteriorate catalyst activity and show poisoning. On the contrary, in this case, a metal halide is not present, and catalyst activity is increased and polymerization reaction may be efficiently performed with a small amount used, and the molecular weight of an oligomer and a polymer may be easily controlled.

Particularly, in the step of reacting the organic borate-based compound with the dispersion, reaction as in the following Reaction 1 may be performed:

[Reaction 1]

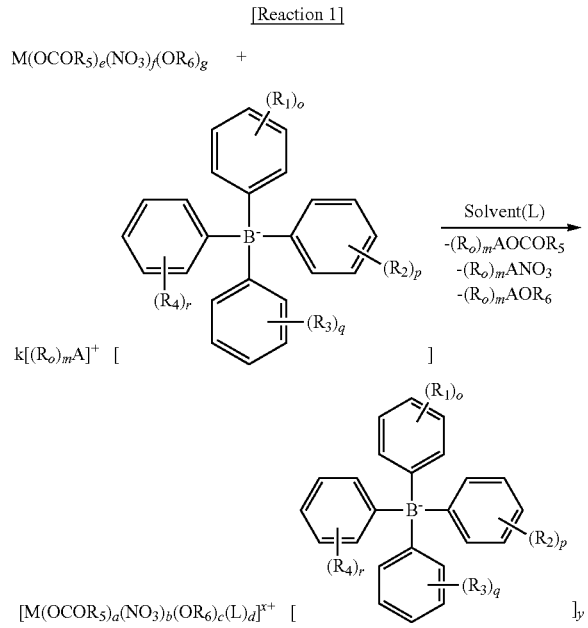

In Reaction 1, the definition of M; L; $R_1$ to R6; a, b, c and d; o, p, q and r; and x and y is the same as described above.

In an embodiment, if a metal carboxylate is used as a metal precursor in the preparation method of the organometal catalyst of the present invention, the reaction of the organic borate-based compound and the dispersion may be performed according to Reaction 2 below. In addition, the metal precursor used in the reaction may have both types of an anhydrous metal compound $M(OCOR_5)_e$ and a hydrated metal compound $(M(OCOR_5)_e$ and a hydrated metal compound $(M(OCOR_5)_e.B(H_2O)$, a=1-3, B=1-10).

[Reaction 2]

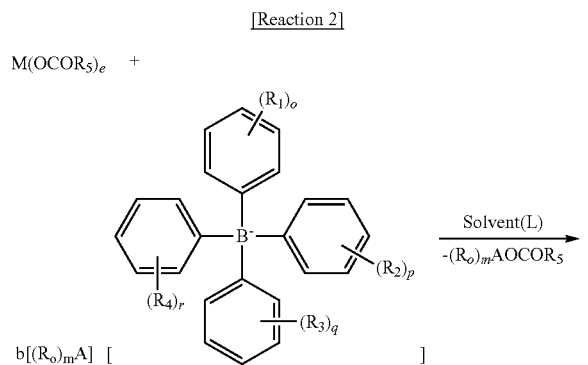

-continued

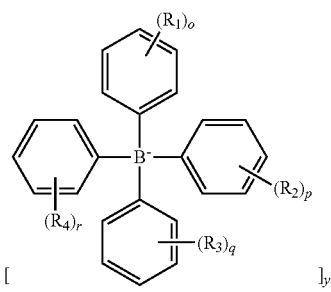

In addition, if a metal nitrate is used as the metal precursor, the reaction of the organic borate-based compound and the dispersion may be performed according to Reaction 3 below. In addition, the metal precursor used in the reaction may have both types of an anhydrous metal compound $M(NO_3)_f$ and a hydrated metal compound $(M(NO_3)f.B(H_2O)$, a=1-3, B=1-10).

[Reaction 3]

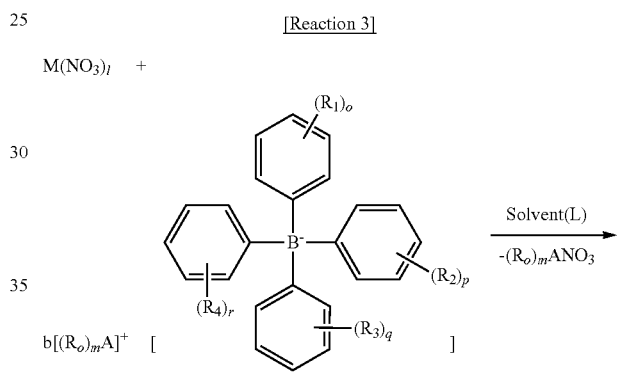

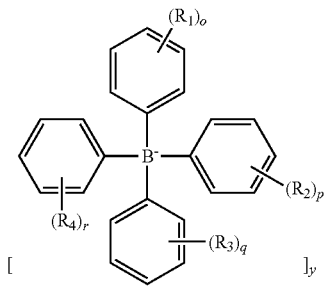

In addition, if a metal hydroxide or alkoxide is used as the metal precursor, the reaction of the organic borate-based compound and the dispersion may be performed according to Reaction 4 be low. In addition, the metal used in the reaction may have both types of an anhydrous metal compound $M(OR_6)_g$ and a hydrated metal compound $(M(OR_6)_g.B(H_2O)$, R=hydrogen, an alkyl group, an aryl group or an allyl group, a=1-3, B=1-10).

[Reaction 4]

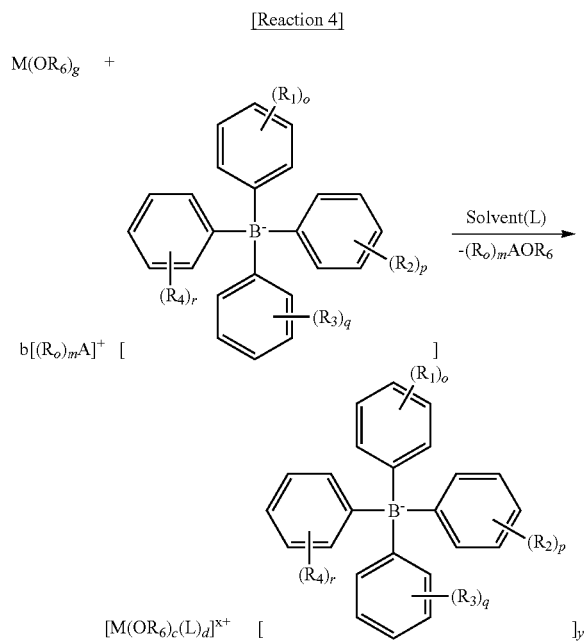

In addition, if a metal halide is used as the metal precursor, the reaction of the organic borate-based compound and the dispersion may be performed according to Reaction 5 below. In addition, the metal used in the reaction may preferably be an anhydrous metal compound $(M(X)_h, X=Cl, Br, I]$ type.

[Reaction 5]

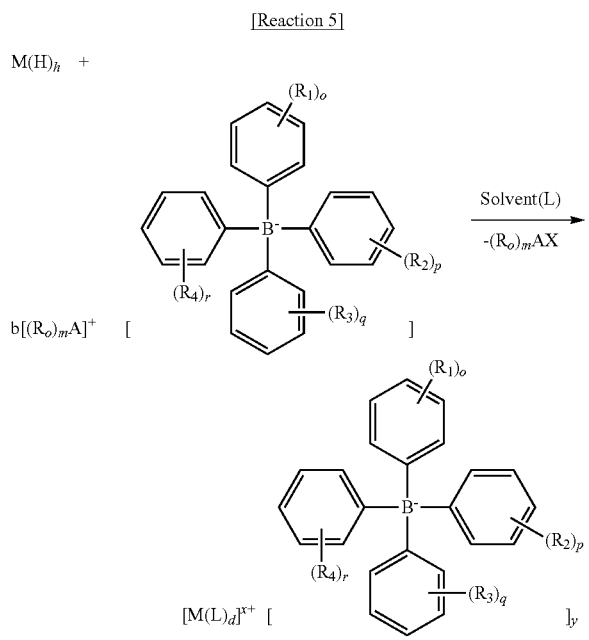

The catalyst prepared by the conventional method surely included a metal halide as a by-product, but the catalyst of the present invention is characterized in being prepared by the above-mentioned reaction and not containing a metal halide, particularly, a halide of one or more metals selected from the group consisting of metals in group 1, group 2 and group 11.

In the reaction step of the present invention, the molar ratio of the metal precursor and the organic borate-based compound may be 1:1 to 1:4, and may be used in an equivalent quantity of a metal salt or alkoxide required to be removed.

In addition, the reaction step may be performed by stirring the reactants at room temperature for 2 to 5 hours.

The method for preparing an organometal catalyst may further include a step of dissolving the organic borate-based compound in a coordinating solvent or a non-coordinating solvent prior to reacting with the dispersion. There is no problem if the amount of the organic borate-based compound is small, but if a large amount is prepared and the reaction is undergone without being dissolved in a solvent, side reactions may arise due to heating, and yield may decrease.

In this case, the amount of the coordinating solvent or the non-coordinating solvent is not limited. However, the total amount of the coordinating solvent in the reaction step is preferably controlled with respect to the metal precursor to achieve a molar ratio of at least 1:4, at least 1:6, at least 1:8, at least 1:10, at least 1:12, at least 1:16, or at least 1:18.

For example, the molar ratio of the organic borate-based compound with the coordinating solvent or non-coordinating solvent may be 1:2 to 1:5, or 1:7 to 1:10.

In addition, the method for preparing the organometal catalyst may further include a step of adding a coordinating solvent to the reactant after the step of reacting the organic borate-based compound with the dispersion.

In addition, the method for preparing the organometal catalyst may further include a step of washing the catalyst obtained in the reaction step with an organic solvent or distilling. For example, $(R_O)_3AOCOR$, $(R_O)_3ANO_3$ or $(R_O)_3AOR$ (A=C or Si, $R_O$=each independently hydrogen, an alkyl group, an alkoxy group, an aryl group or an aryloxy group, and R=hydrogen, alkyl, aryl or allyl) produced in the reaction step may be easily simply removed by washing with an organic solvent or distilling. In case of using an amine-based borate, HOAc or $HNO_3$ produced together with aniline may be also easily removed through washing or distilling.

The organic solvent may include one or more selected from the group consisting of a linear alkyl solvent, for example, pentane, cyclopentane, hexane, cyclohexane, heptane, or octane, and an ether solvent, for example, diethyl ether, or petroleum ether.

In the method for preparing a butene oligomer of the present invention, a step for removing the organometal catalyst by washing a oligomerized product after performing the step of oligomerizing, is not separately conducted. Instead, the catalyst may be easily removed by filtering the polymerizing product into a low product.

The filtering may be performed using a filter including one or more selected from the group consisting of porous materials, for example, celite, silica, zeolite and alumina. In this case, the catalyst is thought to be filtered through an absorption principle of the porous material, etc. Accordingly, in case of using a glass fiber or a filter having a minute pore size, catalyst filtering efficiency may be degraded.

The method for preparing a butene oligomer of the present invention may further include a step of drying remaining solvents after the filtering step.

For example, the drying temperature may be 30 to 200° C., or 40 to 150° C., and the vacuum degree may be 300 torr or less, 200 torr or less, or 100 torr or less. Hereby, a desired butene oligomer may be efficiently obtained. In addition, the drying method is not specifically limited and may be conducted by common methods.

In addition, in the method for preparing a butene oligomer of the present invention, a step of drying a halogenated hydrocarbon solvent may be separately conducted or not after the step of oligomerizing and prior to filtering. In case of conducting the drying step, the drying conditions may be the same as described above, without specific limitation.

In case of separately conducting the drying step of the halogenated hydrocarbon solvent, there are advantages of obtaining a butene oligomer with even higher purity. However, according to the present invention, the catalyst may be easily removed through simple filtering as described above, and a separate drying step of the halogenated hydrocarbon solvent after the step of oligomerizing and prior to filtering, may be omitted, and there are advantages of simplifying processes.

2. Butene Oligomer

Another embodiment of the present invention provides a butene oligomer prepared according to the method for preparing a butene oligomer.

The oligomerizing step may be conducted by batch type or continuous type in the present invention, and the number average molecular weight range and polydispersity (PDI) of the butene oligomer obtained may be different according to the process.

For example, the number average molecular weight of the butene oligomer may be 5,500 or less, or 4,500 or less, or 4,200 or less, or 3,900 or less, or 3,500 or less, and 500 or more, or 750 or more, or 1000 or more, or 1200 or more.

In addition, the polydispersity (PDI) of the oligomer may be 1.5 to 3, or 1.8 to 2.5.

In addition, the exo-content of the butene oligomer prepared by the preparation method may have the exo-content of 50 to 99%, preferably, 74 to 99%, preferably, 80 to 99%, preferably, 89 to 98%, preferably, 94 to 98%. The exo-content represents a case where a carbon-carbon double bond is positioned at the terminal of a polyolefin, and if the exo-content increases, it means that high reactive polyolefin, for example, high reactive polybutene (HR-PB) is produced well.

If the reaction time for oligomerizing using the catalyst is increased, the exo-content tends to decrease due to the structural isomerization reaction of the butene oligomer. This is a limit generated due to the reaction with the butene oligomer because the catalyst is dissolved in the reaction product all the time. However, according to the preparation method of the present invention, a mixture solvent of the halogenated hydrocarbon solvent and the nonpolar hydrocarbon solvent is used, and the dissolution phenomenon of the catalyst in the solvent may decrease. Accordingly, the limit of decreasing the exo-content as described above may be solved.

EXAMPLES

Hereinafter, embodiments of the present invention will be described in detail so as to assist the understanding of the present invention. However, the embodiments below are only illustrations, and the invention may be changed and modified in many different forms and should not be construed as being limited to the embodiments set forth herein, and such change and modification should be included in attached claims.

Preparation Example 1

<Preparation of Organometal Catalyst>

In a glove box, 100 mg of Al(OH)$_2$(OAc) (purchased from Sigma-Aldrich) was put into a vial together with a magnetic bar, and 2 ml of an acetonitrile solvent was added thereto. To another vial, 3 equivalents of [Et$_3$Si]$^+$[B(C$_6$F$_5$)$_4$](purchased from Asahi Glass Co.) of the metal precursor was put, and 3 ml of an acetonitrile solvent was also added thereto for dissolving. To an Al precursor solution while stirring, [Et$_3$Si]$^+$[B(C$_6$F$_5$)$_4$] dissolved in acetonitrile was slowly added. Then, stirring was performed at room temperature for 5 hours. After removing all solvents in vacuum, washing was performed with benzene and hexane. The remaining material was sufficiently dried in vacuum to obtain a transition metal complex as a powder type.

Example 1

<Polymerization of Butene Oligomer-Batch Type Reaction>

An andrew glass pressure reactor from which moisture and oxygen were removed was prepared. 20 g of isobutylene was injected through a line connected with an isobutylene bombe and the andrew glass. A mixture solvent of 20 ml of hexane and 60 ml of dichloromethane (DCM) was used as a solvent after storing in molecular sieve to remove moisture, and was injected after calculating monomer concentration in the reactant (total solution for compound, TSC) from the top of the andrew glass using a syringe. After finishing the injection of the solvent and the monomer, the Andrew glass was moved into a water bath, and the temperature was set to the polymerization temperature of 30° C.

0.01 wt % of the catalyst of Preparation Example 1 stored at a low temperature in a glove box was weighed based on the total weight of the monomer and dissolved in a DCM solvent. The resultant solution was transported to a pressure syringe and moved out of the glove box. To a reactor, argon was pressurized to 2 or 3 bar, and the catalyst was injected. From the moment of injecting the catalyst as the reaction starting point, polymerization reaction to a low polymer was carried out to proceed the reaction until the pressure became 0 bar or for 2 hours. After finishing the reaction, a valve at the top of the andrew glass was opened, remaining unreacted isobutylene was removed, and the andrew glass was opened to recover a polymer and a solvent. The remaining solvents of the recovered solution was removed through a rotary evaporator to obtain a polymer.

Examples 2 and 3, and Comparative Examples 1 to 3

Butene oilgomers of Examples 2 and 3, and Comparative Examples 1 and 2 were prepared by using the catalyst of Preparation Example 1 and changing solvent amount conditions as shown in Table 1 below. In addition, as Comparative Example 3, boron trifluoride diethyl etherate (BF$_3$DEE) of Aldrich Co. was purchased and used.

Example 4

<Polymerization of Butene Oligomer-Continuous Type Reaction>

A reactor was sufficiently purged with argon to remove moisture and oxygen. The remaining amount was checked if isobutylene and solvents were sufficiently prepared, and solvents were set to be continuously injected in a ratio of 33 wt % of hexane and 67 wt % of DCM.

0.01 wt % of the catalyst of Preparation Example 1 stored at a low temperature in a glove box was weighed based on the total weight of the monomer, dissolved in DCM and transported to a catalyst tank. The isobutylene and solvents were injected into the reactor, and at the same time the catalyst was injected into the reactor. After securing if the catalyst and raw materials were injected well, the recording of a reaction initiation time was started. A gear pump at the rear of the reactor and a back-pressure regulator (BRP) were controlled to maintain a reactor level in line with a preset retention time. After achieving stabilization, a sample was taken and solvents were removed to obtain a polymer.

Examples 5 and 6, and Comparative Examples 4 to 6

Butene oilgomers of Examples 5 and 6, and Comparative Examples 4 to 6 were prepared by using the catalyst of Preparation Example 1 and changing solvent amount conditions as shown in Table 2 below.

Experimental Example 1

<Exo Content and Number Average Molecular Weight>

The exo content and number average molecular weight value of the butene oligomers thus obtained were measured as follows and shown in Table 1:

① Exo content: exo-olefin and endo-olefin types were secured according to the position of a double bond by measuring 1H NMR using Varian 500 MHz NMR, and the exo-content (%) was calculated according to the following equation:

Exo-content (%)=(exo-olefin content where carbon-carbon double bond is positioned at terminal/total content of exo-olefin and endo-olefin obtained)*100

② Number average molecular weight: the oligomers thus produced were measured under the following gel permeation chromatography (GPC) analysis conditions:

Column: PL MiniMixed B×2
Solvent: THF
Flow rate: 0.3 ml/min
Specimen concentration: 2.0 mg/ml
Injection amount: 10 μl
Column temperature: 40° C.
Detector: Agilent RI detector
Standard: polystyrene (corrected by a cubic function)
Data processing: ChemStation

TABLE 1

| | Catalyst | Hexane (mL) | DCM (mL) | Exo-content (%) | Mn |
|---|---|---|---|---|---|
| Example 1 | Preparation Example 1 | 20 | 60 | 92 | 4,390 |
| Example 2 | | 40 | 40 | 91 | 4,470 |
| Example 3 | | 60 | 20 | 92 | 2,320 |
| Comparative Example 1 | | 0 | 80 | 56 | 7,040 |
| Comparative Example 2 | | 80 | 0 | — | — |
| Comparative Example 3 | BF$_3$DEE purchased and used | 40 | 40 | — | — |

From the results of Examples 1 to 3, it could be confirmed that a butene oligomer having a low molecular weight and high exo-content was obtainable by using a mixture solvent of a halogenated hydrocarbon solvent and a nonpolar hydrocarbon solvent by performing a batch type process. Particularly, the exo-content was at least 91%, and the number average molecular weight was in a range of 4,500 or less. On the contrary, Comparative Example 1 corresponds to a case of using a DCM solvent solely, and the catalyst was dissolved in the solvent all the time, a portion of the product reacted with the catalyst to generate structural isomerization phenomenon, and a butene oligomer having the low exo-content was considered to be obtained. In addition, according to Comparative Example 1, the number average molecular weight was greater than 5,500, and a butene oligomer having a higher molecular weight than the Examples was obtained.

Meanwhile, Comparative Example 2 corresponded to a case of using hexane only as the solvent, and oligomerization reaction was not smooth and a butene oligomer was not obtained.

In addition, in case of Comparative Example 3, the reaction was explosively carried out in the same temperature conditions as in Example 1, and a butene oligomer was not obtained. Meanwhile, though polymerization was performed using the catalyst of Comparative Example 3 at a low temperature in a range of −30-0° C., a butene oligomer in a high molecular weight range was produced, and it is expected that a low molecular weight oligomer as in the present invention was not produced.

TABLE 2

| | | Hydrocarbon solvent | | | Exo- | |
| | Catalyst | Kind | Amount (wt %) | DCM (wt %) | content (%) | Mn |
|---|---|---|---|---|---|---|
| Example 4 | Preparation Example 1 | Hexane | 33 | 67 | 90 | 2,030 |
| Example 5 | | Toluene | 33 | 67 | 92 | 2,040 |
| Example 6 | | Hexane | 60 | 40 | 92 | 1,850 |
| Comparative Example 4 | | — | 0 | 100 | 59 | 1,230 |
| Comparative Example 5 | | Hexane | 100 | 0 | — | — |
| Comparative Example 6 | | Toluene | 100 | 0 | 78 | 1,040 |

From the results of Examples 4 to 6, it could be confirmed that a butene oligomer having a low molecular weight and high exo-content was obtainable by using a mixture solvent of a halogenated hydrocarbon solvent and a nonpolar hydrocarbon solvent by performing a continuous type process. Particularly, an oligomer having the exo-content of at least 90%, the number average molecular weight in a range of 1,850 to 2,040, and a lower molecular weight range when compared to the batch process of Examples 1 to 3, was obtained. Particularly, Examples 4 and 5 are cases in which the mixing ratio of the halogenated hydrocarbon solvent and the nonpolar hydrocarbon solvent was about 2:1, and the number average molecular weight was maximally 2,040. Meanwhile, in case of Comparative Example 4 using only DCM, very low exo-content was shown. In addition, in case of Comparative Example 5 using only hexane, the oligomerizing reaction was not performed smoothly, and a butene oligomer was not obtained. In case of Comparative Example 6 using only toluene, the reactivity was high, the removal of heat was difficult, and side reactions were increased, and accordingly, a butene oligomer having the low exo-content was obtained.

Experimental Example 2

<Removal of Catalyst from Polymerized Butene Oligomer>

In Examples 2, 5 and 6, the reaction solution after the oligomerization reaction was passed as it was through columns including celite, silica and zeolite and glass fiber as shown in Table 3 below, respectively, without removing residual solvents.

With respect to cases of performing filtering by passing through four columns for Examples 2, 5 and 6, and cases of not performing filtering for Examples 2, 5 and 6 and Comparative Example 1, IC analysis was performed according to the methods below, and the results are shown in Table 3 below.

① F analysis: Combustion IC (ICS-5000/AQF-2100H)

1.1. Combustion IC Analysis Conditions

1) Column: IonPac AS18 analytical (4×250 mm), IonPac AG18 guard (4×50 mm)

2) Eluent kind: KOH (30.5 mM)

3) Eluent flow rate: 1 mL/min

4) Detector: Suppressed Conductivity Detector

5) SRS Current: 76 mA

6) Injection Volume: 20 µl

7) Isocratic/Gradient conditions: Isocratic 1.2. Combustion IC Analysis Method

1) In case of measuring by injecting a specimen once: measurement detection limit 10 mg/kg 2) in case of measuring after injecting a specimen five times and concentrating: measurement detection limit 2 mg/kg

TABLE 3

| Polymerization method | Filtering method | | | | Elemental analysis result [mg/kg] F |
|---|---|---|---|---|---|
| | Celite | Silica | Zeolite | Glass fiber | |
| Example 2 | O | X | X | X | <10 |
| | X | O | X | X | <10 |
| | X | X | O | X | <10 |
| | X | X | X | O | 49 |
| | X | X | X | X | 48 |
| Example 5 | O | X | X | X | <10 |
| | X | O | X | X | <10 |
| | X | X | O | X | <10 |
| | X | X | X | O | 35 |
| | X | X | X | X | 35 |
| Example 6 | O | X | X | X | <10 |
| | X | O | X | X | <10 |
| | X | X | O | X | <10 |
| | X | X | X | O | 39 |
| | X | X | X | X | 40 |
| Comparative Example 1 | X | X | X | X | 47 |

From the results, it could be confirmed that the catalyst may be easily removed by performing filtering with respect to the reaction solution after the oligomerizing step of the present invention. Particularly, it was confirmed that if filtering was performed with columns including celite, silica and zeolite for Examples 2, 5 and 6, a trace amount of F element component was detected, and thus, the catalyst was removed well.

Meanwhile, if filtering was not performed for Examples 2, 5 and 6 and Comparative Example 1, it was confirmed that F element component was detected to a certain degree or more, and the catalyst was remained. In addition, in case of using a column including glass fiber, similar degree of F element component was detected as in the case of not performing filtering, and accordingly, it could be confirmed that the filtering was not performed well.

The invention claimed is:

1. A method for preparing a butene oligomer, the method comprising:
   a step of oligomerizing a polymerization solution comprising a halogenated hydrocarbon solvent, a nonpolar hydrocarbon solvent and an isobutene monomer, in the presence of an organometal catalyst represented by the following Formula 1:

[Formula 1]

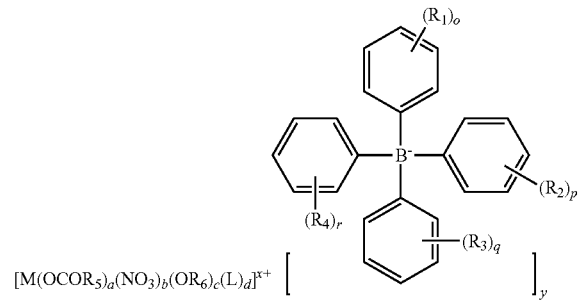

in Formula 1,

M is selected from the group consisting of metals in group 13 and lanthanide series, L is each independently a coordinating solvent molecule comprising a functional group selected from the group consisting of a cyanide group, an isocyanide group, an ether group, a pyridine group, an amide group, a sulfoxide group and a nitro group, $R_1$ to $R_4$ are each independently hydrogen, a halogen group, or a substituted or unsubstituted C1-C20 alkyl group, $R_5$ and $R_6$ are each independently hydrogen, a C1-C20 alkyl group, a C6-C20 aryl group, or an allyl group, a, b, c and a+b+c are each independently an integer of 0 to 3, d and a+b+c+d are each independently an integer of 1 to 10, o, p, q and r are each independently an integer of 1 to 5, and x and y are an integer of 1 to 4 and are the same.

2. The method for preparing a butene oligomer according to claim 1, wherein a volume ratio of the halogenated hydrocarbon solvent and the nonpolar hydrocarbon solvent is 25:75 to 99:1.

3. The method for preparing a butene oligomer according to claim 1, wherein the halogenated hydrocarbon solvent is one or more selected from the group consisting of chloromethane, dichloromethane, trichloromethane, 1-chlorobutane and chlorobenzene.

4. The method for preparing a butene oligomer according to claim 1, wherein the nonpolar hydrocarbon solvent is one or more selected from the group consisting of butane, pentane, neopentane, hexane, cyclohexane, methylcyclohexane, heptane, octane, benzene, toluene, xylene, and ethylbenzene.

5. The method for preparing a butene oligomer according to claim 1, wherein the step of oligomerizing is performed by a batch type or continuous type process.

6. The method for preparing a butene oligomer according to claim 1, further comprising a step of removing the organometal catalyst by filtering an oligomerized product.

7. The method for preparing a butene oligomer according to claim 6, wherein the filtering is performing using a filter comprising one or more selected from the group consisting of celite, silica, zeolite and alumina.

8. The method for preparing a butene oligomer according to claim 6, wherein a step of drying the halogenated hydrocarbon solvent is not performed after the step of oligomerizing and prior to filtering.

9. The method for preparing a butene oligomer according to claim 1, wherein a step of washing an oligomerized product to remove the organometal catalyst is not performed.

10. The method for preparing a butene oligomer according to claim 1, wherein
M is one or more selected from the group consisting of Al, Ga, In, Tl, La, Ce, Pr, Nd, Pm, Sm, Eu, Gd, Tb, Dy, Ho, Er, Tm, Yb and Lu;
L is one or more selected from the group consisting of acetonitrile, propionitrile, 2-methylpropanenitrile, trimethylacetonitrile, benzonitrile, dialkyl ether, pyridine, dimethylformamide, dimethyl sulfoxide, nitromethane, nitrobenzene and the derivatives thereof, and a coordinating solvent molecule in which an unshared electron pair of oxygen, nitrogen or carbon makes a coordination bond with M;
$R_1$ to $R_4$ are each independently hydrogen, a halogen group, or a halogen-substituted C1-C12 alkyl group, and
$R_5$ and $R_6$ are each independently hydrogen, a C1-C12 alkyl group, a C6-C12 aryl group, or an allyl group.

11. The method for preparing a butene oligomer according to claim 1, wherein the organometal catalyst does not comprise a halogen salt of one or more metals selected from the group consisting of metals of group 1, group 2 and group 11.

12. The method for preparing a butene oligomer according to claim 11, wherein the halogen salt is one or more selected from the group consisting of silver chloride (AgCl), lithium chloride (LiCl), sodium chloride (NaCl), potassium chloride (KCl), magnesium chloride ($MgCl_2$), silver bromide (AgBr), lithium bromide (LiBr), sodium bromide (NaBr), potassium bromide (KBr), magnesium bromide ($MgBr_2$), silver iodide (AgI), lithium iodide (LiI), sodium iodide (NaI), potassium iodide (KI) and magnesium iodide ($MgI_2$).

13. The method for preparing a butene oligomer according to claim 1, wherein the borate-based bulky anion of the organometal catalyst represented by Formula 1 is one or more selected from the group consisting of tetrakis(phenyl)borate, tetrakis(pentafluorophenyl)borate, tetrakis [3,5-bis (trifluoromethyl)phenyl]borate, and the derivatives thereof.

14. The method for preparing a butene oligomer according to claim 1, wherein the butene oligomer produced by the oligomerization has a number average molecular weight of 500 to 5,500.

15. The method for preparing a butene oligomer according to claim 1, wherein the isobutene monomer is included in an amount of 1 to 50 wt % based on the total weight of the polymerization solution.

16. The method for preparing a butene oligomer according to claim 1, wherein the butene oligomer produced by the oligomerization has a polydispersity (PDI) of 1.5 to 3, and an exo-content of 50% to 99%.

* * * * *